| United States Patent [19] | [11] 3,991,199 |
|---|---|
| Berger | [45] Nov. 9, 1976 |

[54] PYRIDOINDOLES

[75] Inventor: Joel G. Berger, Freeport, N.Y.

[73] Assignee: Endo Laboratories, Inc., Garden City, N.Y.

[22] Filed: Nov. 8, 1974

[21] Appl. No.: 522,145

Related U.S. Application Data

[63] Continuation-in-part of Ser. No. 422,613, Dec. 9, 1973, abandoned.

[52] U.S. Cl. .......................... 424/267; 260/240 K; 260/293.55
[51] Int. Cl.² ................................. C07D 471/04
[58] Field of Search ............... 260/293.55, 240 K; 424/267

[56] References Cited
UNITED STATES PATENTS

3,657,254  4/1972  Barkov et al. ............... 260/293.55
3,812,135  5/1974  Okamoto et al. ............. 260/293.55

OTHER PUBLICATIONS

Heath–Brown, Chemistry and Industry, 1969, pp. 1595–1596.
Fieser et al., Advanced Organic Chemistry, pp. 92–104, N.Y., Reinhold, 1961.

*Primary Examiner*—Natalie Trousof

[57] ABSTRACT

Certain trans-2,3,4,4a,5,9b-hexahydro-1H-pyrido-[4,3-b]indoles useful as analgesics and sedatives. Some are also useful as major (antipsychotics) and/or minor (anxiolytics) tranquilizers, muscle relaxants, or hypotensives. The compounds of this invention are made by borane/THF reduction of $\Delta^{4a,9b}$-tetrahydro precursors, followed where necessary by dealkylation, alkylation and/or acylation/reduction.

18 Claims, No Drawings

PYRIDOINDOLES

CROSS-REFERENCE TO RELATED APPLICATION

This is a continuation-in-part of my copending application Ser. No. 422,613, filed Dec. 6, 1973 now abandoned.

BACKGROUND OF THE INVENTION

This invention relates to pharmaceutically useful 2,3,4,4a,5,9b-hexahydro-1H-pyrido[4,3-b]indoles.

Barkov et al., U.S. Pat. No. 3,657,254 discloses the compound of the formula which, according to IUPAC nomenclature, is 2,8-dimethyl-2,3,4,4a,5,9b-hexahydro-1H-pyrido[4,3-b]]indole. Because of the method of production, the hydrogen atoms attached to the carbons in the 4a and 9b positions were in cis-relation. The patent discloses that the compound has psychotropic effects, specifically neuroleptic, antidepressive, and energizing effects, and that the mechanism of action is by adrenergic blockade.

Heath-Brown, Chem. Ind. (London) p. 1595-6, 1969, discloses 2,3,4,4a,5,9b-hexahydro-2-methyl-5-phenyl-1H-pyrido[4,3-b]indole hydrochloride. The hydrogen atoms attached to the 4a and 9b carbon atoms were in cis-relation to each other, because of the reduction method (Na/liq.NH$_3$) used. No utility for the compound is disclosed in the reference.

SUMMARY OF THE INVENTION

This invention is a class of novel trans-2,3,4,4a,5,9b-hexahydro-1H-pyrido[4,3-b]indoles of the formula:

and their pharmaceutically suitable salts, where the hydrogens attached to the carbon atoms in the 4a and 9b positions are in trans relationship to each other, and where:

when Y is —H, X is —H, —Cl, —Br, —CH$_3$, -tert-C$_4$H$_9$ or —OCH$_3$; and when Y is —CF$_3$, X is —H; and R is hydrogen; 3-chloro-2-butenyl; 2-bromoallyl; benzyl; benzyl ring-substituted with methyl, methoxy or chloro; phenethyl; 3-phenylpropyl; 3-phenylpropyl ring-substituted with chloro, bromo, or methoxy; furfuryl; 2-thenyl; C$_1$–C$_5$ alkyl; C$_3$–C$_5$ alkenyl; C$_3$–C$_5$ alkynyl; cinnamyl; cinnamyl ring-substituted with chloro, bromo, or methoxy; 3-phenyl-2-propynyl; C$_3$–C$_7$ cycloalkyl; C$_4$–C$_8$ cycloalkylmethyl; (methylcyclopropyl)methyl; (cis-2,3-dimethylcyclopropyl)methyl; C$_6$–C$_8$ cycloalkenylmethyl; C$_6$–C$_8$ cycloalkadienylmethyl; (2,3-dimethylcycloprop-2-en-1-yl)methyl; exo-7-norcarylmethyl; (cis-1,6-dimethyl-endo-3-norcaren-7-yl)methyl; (4-methylbicyclo[2.2.2]oct-1-yl)methyl; (4-methylbicyclo[2.2.2]oct-2-en-1-yl)methyl; (bicyclo[2.2.2]hept-2-yl)methyl; (bicyclo[2.2.2]hept-2-en-5-yl)methyl; 1-adamantylmethyl; or 2-adamantylmethyl.

The compounds of Formula I are useful as analgesics and sedatives. In addition, some are useful as major or minor tranquilizers, and some are useful as muscle relaxants. Many are useful as hypotensives, presumably through the mechanism of adrenergic blockage.

Preferred compounds of the present invention include those compounds of Formula I where:

X is hydrogen or bromine, and those compounds of Formula I where:

R is hydrogen, 3-chloro-2-butenyl, phenethyl, furfuryl, 2-thenyl, C$_1$–C$_5$ alkyl, allyl, propynyl, C$_3$–C$_5$ cycloalkyl, C$_4$–C$_7$ cycloalkylmethyl, C$_7$ cycloalkenylmethyl, (2,3-dimethylcycloprop-2-en-1-yl)methyl, exo-7-norcarylmethyl, (4-methylbicyclo[2.2.2]oct-1-yl)methyl, (4-methylbicyclo[2.2.2]oct-2-en-1-yl)methyl, 1-adamantylmethyl or 2-adamantylmethyl.

Of course, more preferred compounds of the present invention are those compounds of Formula I where both the variables X and R are taken from within the scope set forth immediately above.

Still more preferred compounds of the present invention are those compounds of Formula I where:

X is hydrogen or bromine and Y is hydrogen, and those compounds of Formula I where:

R is hydrogen, methyl, ethyl, cyclobutylmethyl, cyclopentylmethyl, exo-7-norcarylmethyl, 1-adamantylmethyl or 2-adamantylmethyl.

Of course, more preferred compounds of the present invention are those compounds of Formula I where all three of the variables X, Y, and R are taken from the scope set forth immediately above.

Most preferred compounds of Formula I are:

1. trans-2,3,4,4a,5,9b-hexahydro-5-phenyl-1H-pyrido[4,3-b]indole, because its analgesic activity is separated from its sedative activity by a 10-fold difference in dose.

2. and (3) trans-2-(1-adamantylmethyl)-2,3,4,4a,5,9b-hexahydro-5-phenyl-1H-pyrido[4,3-b]indole and trans-2-(2-adamantylmethyl)-2,3,4,4a,5,9b-hexahydro-5-phenyl-1H-pyrido[4,3-b]indole, because they exhibit minor tranquilizing (anxiolytic) activity at doses which are not sedating. They also exhibit major tranquilizing (antipsychotic) activity.

4. trans-2,3,4,4a,5,9b-hexahydro-2-(exo-7-norcarylmethyl)-5-phenyl-1H-pyrido[4,3-b]indole, because of its potency in reducing locomotor activity.

5. (6), (7), and (8) trans-2-ethyl-, trans-2-cyclobutylmethyl)- and trans-2-(cyclopentylmethyl)-2,3,4,4a,5,9b-hexahydro-5-phenyl-1-H-pyrido[4,3-b]indole, and trans-8-bromo-5-(4-bromophenyl)-

2,3,4,4a,5,9b-hexahydro-2-methyl-1H-pyrido[4,3-b]indole because of their major tranquilizer (antipsychotic) activity.

The invention includes pharmaceutical compositions consisting essentially of a pharmaceutically suitable vehicle and means for producing an analgesic effect selected from compounds of Formula I, and a method for producing an analgesic effect in a warm-blooded animal comprising administering an effective amount of an analgesic compound of Formula I. The invention also includes processes for making the compounds of Formula I, described hereinbelow.

DESCRIPTION OF THE INVENTION

Synthesis of the Compounds

Each of the compound of Formula I can be made by one or more of reactions or reaction series (1)-(4).

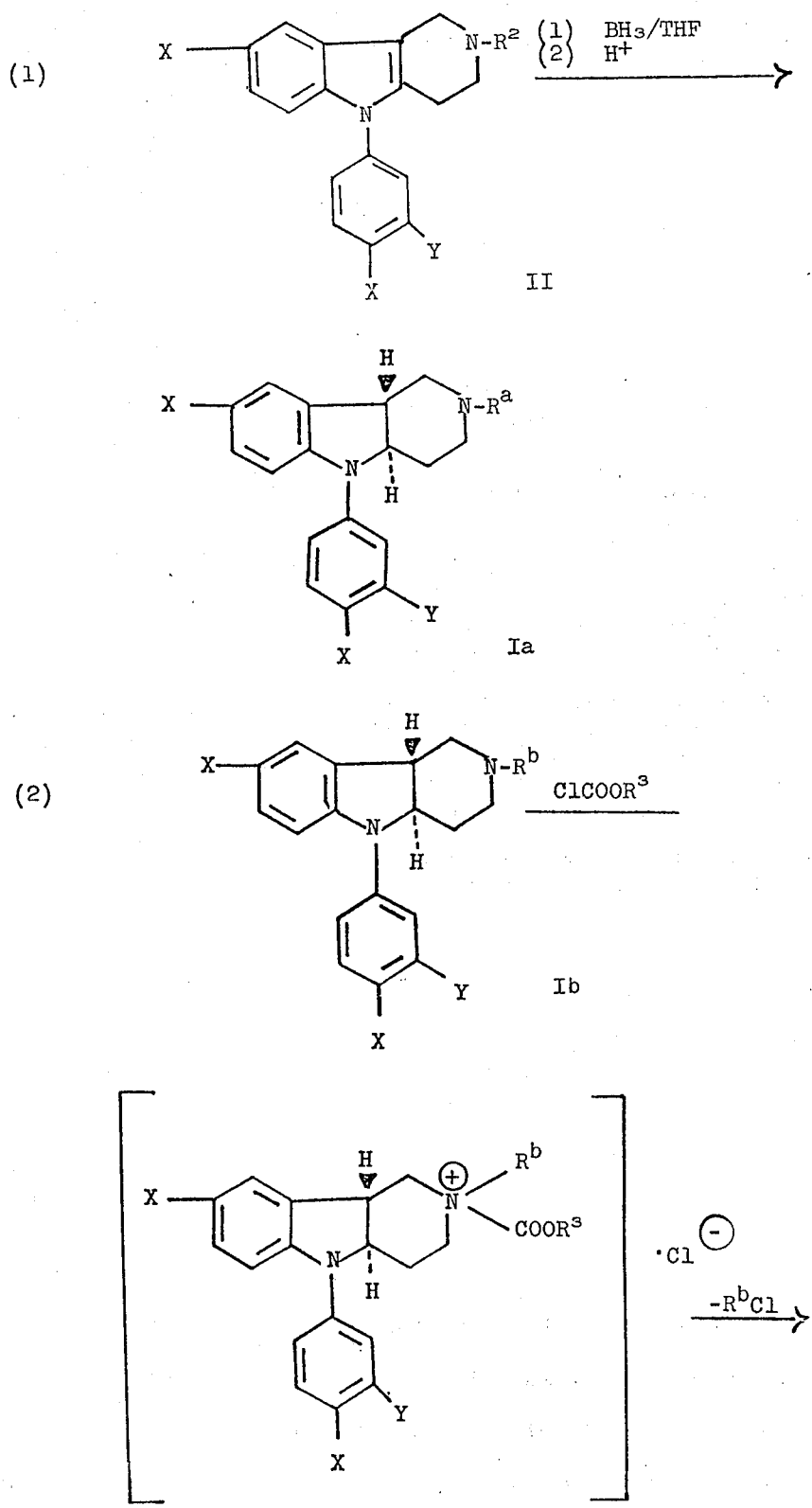

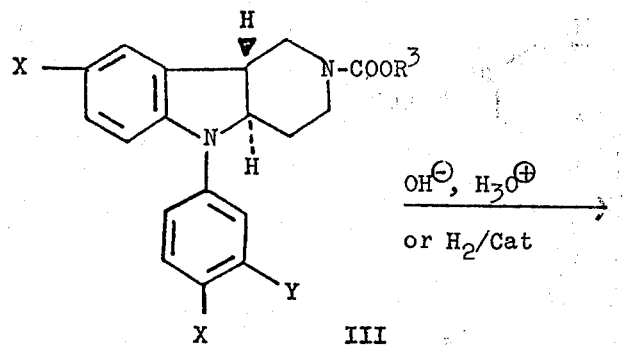
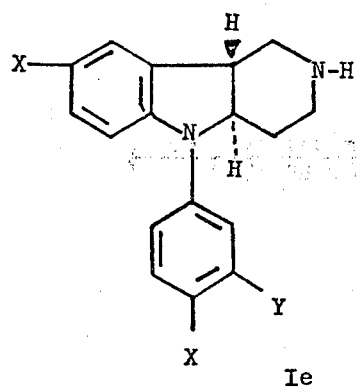
(3)
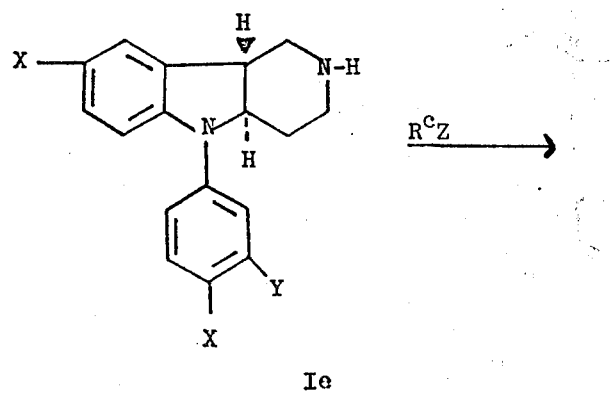
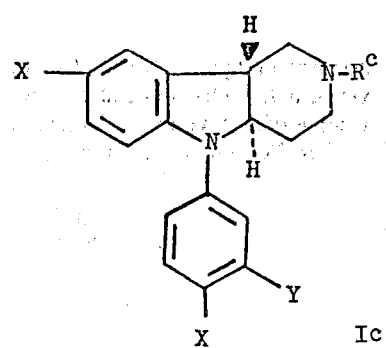

(4)   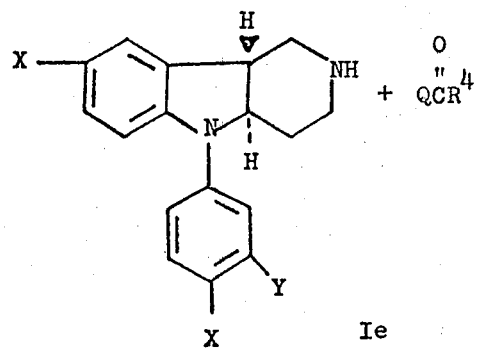

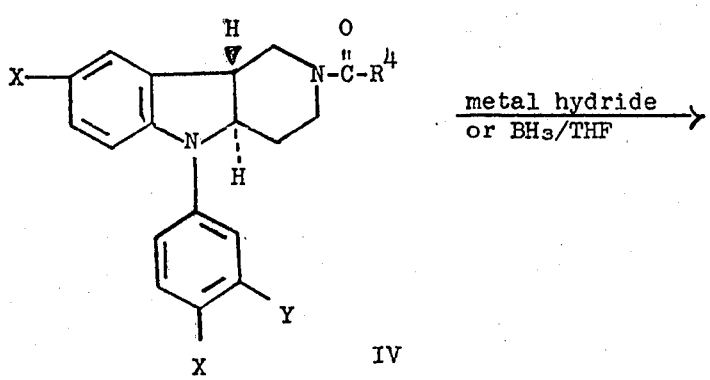

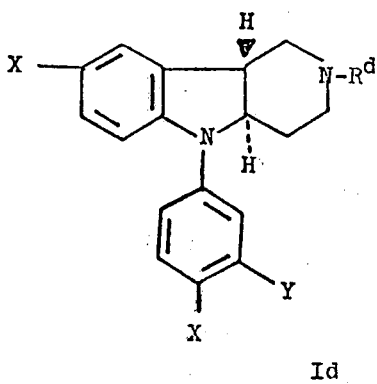

In the foregoing formulae, and whenever used herein:

$R^a$ is benzyl; benzyl ring-substituted with methyl, methoxy or chloro; phenethyl; 3-phenylpropyl; 3-phenylpropyl ring substituted with chloro, bromo, or methoxy; furfuryl; 2-thenyl; $C_1$-$C_5$ alkyl; $C_3$-$C_7$ cycloalkyl; $C_4$-$C_8$ cycloalkylmethyl; (methylcyclopropyl)methyl; (cis-2,3-dimethylcyclopropyl)methyl; exo-7-norcarylmethyl; (4-methylbicyclo [2.2.2] oct-1-yl)methyl; (bicyclo[2.2.2] hept-2-yl)methyl; 1-adamantylmethyl; or 2-adamantylmethyl.

$R^2$ is the same as $R^a$ or is

where $R^7$ is the same as $R^4$, excluding $C_2$-$C_4$ alkynyl, 2-chloro-1-propenyl, 1-bromovinyl, and cis-1,6-dimethyl-endo-3-norcaren-7-yl;

$R^b$ is methyl; ethyl; benzyl; benzyl ring-substituted with chloro, methyl or methoxy; or cyclopropylmethyl;

$R^3$ is $C_1$-$C_4$ alkyl; vinyl; benzyl; p-methylbenzyl; p-methoxybenzyl; or phenyl;

$R^c$ is the same as R, excluding hydrogen, tert-butyl, and cyclopropyl;

$R^4$ is 2-chloro-1-propenyl; 1-bromovinyl; phenyl; chlorophenyl; methylphenyl; methoxyphenyl; benzyl; phenethyl; phenethyl ring-substituted with chloro, bromo, or methoxy; 2-furyl; 2-thienyl; hydrogen; $C_1$-$C_4$ alkyl; $C_2$-$C_4$ alkenyl; $C_2$-$C_4$ alkynyl; $C_3$-$C_7$ cycloalkyl; methylcyclopropyl; $C_5$-$C_7$ cycloalkenyl; $C_5$-$C_7$ cycloalkadienyl; 2,3-dimethycycloprop-2-en-1-yl; exo-7-norcaryl; cis-1,6-dimethyl-endo-3-norcaren-7-yl; 4-methylbicyclo[2.2.2]oct-1-yl; bicyclo[2.2.2]hept-2-yl; 4-methylbicyclo[2.2.2]oct-2-en-1-yl; bicyclo[2.2.2]hept-2-en-5-yl; 1-adamantyl; or 2-adamantyl;

$R^d$ is the same as R, excluding hydrogen; 3-chloro-2-butenyl; 2-bromoallyl; tert-butyl; $C_3$-$C_5$ alkenyl; $C_3$-$C_5$ alkynyl; cinnamyl; cinnamyl ring-substituted with chloro, bromo, or methoxy; 3-phenyl-2-propynyl; $C_3$-$C_7$ cycloalkyl; and $C_6$-$C_8$ cycloalkadienylmethyl; provided, however, that when the reducing agent in reaction series (4) is BH$_3$/THF, the following substituents are also excluded:

$C_6$-$C_8$ cycloalkenylmethyl; (2,3-dimethylcycloprop-2-en-1-yl)methyl; (cis-1,6-dimethyl-endo-3-norcaren-7-yl)methyl; (4-methylbicyclo[2.2.2]oct-2-en-1-yl)methyl; and (bicyclo[2.2.2]hept-2-en-5-yl)methyl; but, when the reducing agent in reaction series (4) is a metal hydride, (cis-2,3-dimethylcyclopropyl)methyl is also excluded; Q is —Cl, —Br, $C_1$-$C_4$ alkoxy;

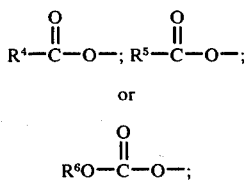

$R^5$ is different from $R^4$ and is $C_1$-$C_4$ alkyl, provided that when $R^4$ is hydrogen, $R^5$ is methyl;

$R^6$ is $C_1$-$C_4$ alkyl;

Z is —Cl; —Br; —I; or —OS(O)$_2R^8$;

$R^8$ is CH$_3$, phenyl, or p-tolyl; and $R^cZ$ can also be $R^9$OS(O)$_2OR^9$, where $R^9$ is $C_1$-$C_4$ alkyl.

Starting Materials

Reaction (1) starts with a 5-phenyl-2,3,4,5-tetrahydro-1H-pyrido[4,3-b]indole (Formula II). Each of reactions or reaction series (2)–(4) starts with a compound of Formula I and converts it to another compound of Formula I.

The Formula II starting materials are made by the Fischer Indole Synthesis, an acid catalyzed condensation between 4-piperidone or a 1-substituted 4-piperidone and a 1,1-diphenylhydrazine, according to the general procedure disclosed in Hörlein, U.S. Pat. No. 2,786,059 and Hörlein, Chem. Ber. 87, 463 (1954) followed (in the case of the unsubstituted 4-piperidone) by conventional alkylation or acylation.

The compound 1,1-diphenylhydrazine is commercially available. The substituted 1,1-diphenylhydrazines can be made by reacting the corresponding 1,1-diarylamine with sodium nitrite and hydrochloric acid in dimethylformamide at about 10° C. to produce an N-nitrosodiphenylamine, then adding the N-nitroso compound in tetrahydrofuran to a suspension of lithium aluminum hydride in dry ether under nitrogen and maintaining the temperature at 25°–35° C. for about 1½ hours. The procedure is analogous to that given for preparation of N-amino-iminodibenzyl in Cohen et al., U.S. Pat. No. 3,457,271.

Alternatively, the N-nitrosodiphenylamine can be condensed directly with the substituted 4-piperidone by contacting the compounds with metallic zinc in presence of glacial acetic acid and ethanol and maintaining the reaction mixture at a temperature of 20°–25° C. for several hours. Thereafter the liquid is separated from the solid and the liquid is contacted with a strong acid at 50°–80° C.

The substituted diphenylamines can be obtained by the copper catalyzed condensation of a substituted aniline with a substituted halobenzene (the Ullman Synthesis) or substituted acetanilide with a substituted halobenzene followed by hydrolytic removal of the acetyl group (the Goldberg Synthesis) or by the Chapman rearrangement of an N,O-diphenyl-benzimidate to an N,N-diphenyl-benzamide, followed by hydrolytic removal of the benzoyl group. Both the Ullman Synthesis and the Chapman Rearrangement are reviewed by Schulenberg and Archer in Volume 14 of Organic Reactions, John Wiley and Sons, New York, 1956.

With the exception of 1-cyclopropyl-4-piperidone and 1-tert-butyl-4-piperidone, the necessary N-substituted 4-piperidones can be made simply by alkylation of 4-piperidone or acylation/reduction of the ethylene acetal of 4-piperidone followed by hydrolysis under conventional conditions. The following procedure can be used to make 1-cyclopropyl-1-piperidone:

A mixture of 28.5 g. of cyclopropylamine and 100 g. of ethyl acrylate is stirred at room temperature for 20 hours, and from the reaction mixture diethyl 3,3'-(cyclopropylimino)dipropionate is distilled, b.p. 122°–124° at 0.8 mm/Hg. A solution of 21.3 g. of this diester in 30 ml. benzene is added dropwise to a cooled suspension of 8.0 g. of sodium hydride in a mixture of 150 ml. benzene with 5 ml. ethanol. Soon an exothermic reaction starts, which at first requires occasional cooling; after heat evolution subsides, the reaction mixture is allowed to stand at room temperature overnight. The next morning it is heated on a steam bath for 1 hour, cooled, and decomposed with 20 g. acetic acid and 13.5 g. water. After filtering off the solids, the benzene solution is washed with aqueous bicarbonate, dried over anhydrous sodium sulfate, and stripped to dryness. On cooling the oily product in the refrigerator for three days and triturating with hexane, crystalline ethyl 1-cyclopropyl-4-oxo-3-piperidinecarboxylate is obtained. After refluxing 17.8 g. of this ester in 90 ml. of 6N hydrochloric acid for one hour, and taking the resulting solution down to dryness, the solid residue is triturated with hot isopropyl alcohol to yield 1-cyclopropyl-1-piperidone hydrochloride, m.p. 209°–210°.

1-tert-Butyl-4-piperidone can be made by the procedure of Mistryukov, Aronova and Kucherov, Izvest. Akad. Nauk S.S.S.R., Otdel, Khim, Nauk. 1961, [cf. Chem. Abstr. 55: 27310$^d$ (1961)].

Reaction (1)

Reaction (1), reduction of the tetrahydro precursors of Formula II to the hexahydro compounds of Formula Ia, is usually carried out in tetrahydrofuran with a four- to-five-fold molar excess of boron hydride/tetrahydrofuran (BH$_3$/THF) complex at a temperature as low as 0° C. or a high as the reflux temperature of tetrahydrofuran. In some cases a higher temperature is necessary or desirable, and the tetrahydrofuran solvent is diluted or replaced with a higher boiling ether such as diglyme or dioxane. The reaction temperature generally does not exceed 110° C. After the reduction, the mixture is acidified, for example, with about 4–10 molar hydrochloric acid, heated to about 100° C., allowed to cool, and neutralized with caustic.

The reduction by BH$_3$/THF followed by treatment with acid produces compounds in which the hydrogens attached to the carbons in the 4a and 9b positions are in trans relationship. This has been confirmed by X-ray crystallography on the methiodide of (+)-2,3,4,4a,5,9b-hexahydro-2-methyl-5-phenyl-1H-pyrido[4,3-b]indole.

Reaction Series (2)

Compounds of Formula I wherein R is H (Formula Ie) cannot be produced directly by reduction with BH$_3$/THF followed by treatment with acid of the corresponding tetrahydro compound; the tetrahydro compound is recovered unchanged on attempted reduction with even BH$_3$/THF in diglyme. Consequently, compounds of Formula Ie must be produced from compounds of Formula Ib according to reaction series (2).

In series (2), the compound of Formula Ib is first reacted with a chloroformate ClCOOR$^3$. This reaction can be carried out at a temperature in the range of 20° to 110° C., preferably 90° to 110° C., in an inert organic solvent such as benzene, toluene or dioxane. The quaternary ammonium salt initially produced upon reaction with the chloroformate is not isolated, and the reaction proceeds to the compound of Formula III. The latter compound can, but need not, be isolated. Hydrolysis of the compound of Formula III to produce the Ie compound can be carried out in a C$_{1-5}$ alkanol containing 0-10% water and a hydroxide of potassium, sodium, lithium or calcium, at a temperature in the range of 65°–140° C. Alternatively, it can be carried out in aqueous mineral acid (e.g., acetic or hydrochloric acid) at a temperature in the range of 20°–110° C. The hydrogenolysis, applicable when R$^3$ is benzyl or substituted benzyl, can be carried out 1–3 atmospheres hydrogen pressure, a temperature in the range of 30°–60° C., and a platinum, palladium or Raney nickel catalyst.

Reaction (3)

The reduction with BH$_3$/THF followed by treatment with acid by the method of reaction (1) reduces not only the indolic double bond of the tetrahydro precursor but also any carbonyl group and/or olefinic or acetylenic unsaturation of the R group. Consequently, compounds of Formula I having reducible R groups must be prepared by alkylation or acylation/reduction of the hexahydro compounds wherein R is hydrogen (Formula Ie) according to reaction (3) and reaction series (4). Of course, compounds having nonreducible R groups can also be prepared by these methods, except for those compounds wherein R is hydrogen, tert-butyl or cycloproyl.

Reaction (3) is a conventional alkylation reaction. The reagent R$^c$Z is an organic halide, (Z = Cl, Br or I), sulfate (R$^c$Z=R$^9$OS(O)$_2$OR$^9$) or sulfonate (Z= OS(O)$_2$R$^8$). The reaction is carried out in a polar organic solvent such as dimethylformamide, dimethyl sulfoxide, hexamethylphosphoramide, acetone, methyl ethyl ketone, methanol or ethanol, in the presence of an alkali metal or alkaline earth metal carbonate or bicarbonate, or a tertiary amine, for example pyridine or triethylamine. Reaction temperatures in the range of 0° to 100° C. can be used; preferred range is 20 to 40° C.

Reaction Series (4)

Reaction Series (4) is a conventional acylation/reduction, the acylating agent

is an acid halide (Q = Cl, Br), ester (Q = C$_{1-4}$ alkoxy), anhydride

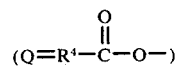

mixed anhydride

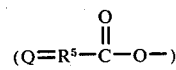

including mixed anhydrides with an ester of carbonic acid

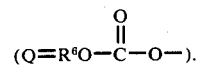

The acylation is carried out in an organic solvent such as benzene, chloroform, or dichloromethane at a temperature of 0° to 80° C., preferably 0° to 40° C. When the acylating agent is an acid halide, an inorganic or tertiary amine base is present to react with liberated acid. The reduction is carried out with a conventional reducing agent such as lithium aluminum hydride in an ethereal solvent, such as tetrahydrofuran, glyme, or diglyme, or sodium bis(2-methoxyethoxy)aluminum hydride in a solvent such as benzene or toluene, at a temperature in the range of 30° to 100° C., preferably 30 to 65° C. Glyme and diglyme are trivial names for ethylene glycol dimethyl ether and diethylene glycol dimethyl ether, respectively. Alternatively, BH$_3$/THF can be used as the reducing agent with essentially the same solvents and under essentially the same reaction conditions.

Compounds of Formula I wherein R is (cis-2,3-dimethylcyclopropyl)methyl can be made by catalytic hydrogenation of a corresponding compound of Formula I wherein R is (2,3-dimethylcycloprop-2-en-1-yl)methyl at temperatures in the range 20°–50° C.

Representative pharmaceutically suitable acids which can be used to make the acid addition salts of this invention are the following: hydrochloric, hydrobromic, sulfuric, sulfamic, phosphoric, nitric, maleic, fumaric, benzoic, ascorbic, citric, pamoic, succinic, methanesulfonic, ethanedisulfonic, acetic, propionic, tartaric, salicyclic, gluconic, lactic, malic, mandelic, cinnamic, citraconic, aspartic, stearic, palmitic, itaconic, glycolic, p-aminobenzoic, glutamic, and toluenesulfonic.

All compounds of Formula I have at least two asymmetric centers, resulting from the reduction of the Δ 4a,9b to the trans-fused system. The invention includes the racemate as well as the individual enantiomers. In addition, if the 2-substituent includes a grouping capable of existing in stereoisomeric forms, all the resulting diastereoisomers are also included in this invention.

Preparation of the compounds of this invention is illustrated by the following examples, wherein all parts, proportions, and percentages are by weight, unless otherwise indicated.

EXAMPLE 1

(+)-trans-2,3,4,4a,5,9b-hexahydro-2-methyl-5-phenyl-1H-pyrido[4,3-b]indole hydrochloride To a solution of 180 ml 1 molar $BH_3$ in THF (0.18 mole $BH_3$) which was cooled in an ice bath, was added a solution of 7.9 grams 2,3,4,5-tetrahydro-2-methyl-5-phenyl-1H-pyrido[4,3-b]indole (0.03 mole) in 200 ml freshly chromatographed THF, dropwise with stirring over 30 minutes in a nitrogen atmosphere. The ice bath was then replaced with a heating mantle and the mixture was refluxed for 19 hours in the nitrogen atmosphere. The mixture was cooled and evaporated under vacuum to a clear gel. The gel was then refluxed in 75 ml of a 1:1 mixture of glacial acetic acid and 5N HCl. A clear light brown solution was obtained after about ½ hour and refluxing was continued for a total of 1 hour. The resulting solution was cooled to about 50° C. and treated with 50% aqueous NaOH until basic, during which time the temperature rose to 80° C. The mixture was cooled again and a light purple oil was extracted into $CHCl_3$. The mixture was again extracted with $CHCl_3$, the extracts were combined and washed with saturated NaCl solution, then dried over $Na_2SO_4$. The $CHCl_3$ was then evaporated under vacuum, leaving a purple oily residue which was taken up in about 50 ml diethyl ether and some ethanol. Ethereal HCl was added and 8.1 grams of pale greenish-white powder were obtained by filtration and drying. Recrystallization from methanol provided 6.2 grams of the title compound, m.p. 256°–258° C.

Using the corresponding compound of Formula II as starting material, and proceeding in a manner similar to that described in Example 1, the illustrative compounds of Formula I listed in Table I can be prepared:

Table I (1) (±)-trans-2-ethyl-2,3,4,4a,5,9b-hexahydro-5-phenyl-1H-pyrido[4,3-b]indole hydrochloride, m.p. 249.5–251° C. (dec)

(2) (±)-trans-2,3,4,4a,5,9b-hexahydro-2-(4-methylbenzyl)-5-phenyl-1H-pyrido[4,3-b]indole (3) (±)-trans-2,3,4,4a,5,9b-hexahydro-2-(4-methoxybenzyl)-5-phenyl-1H-pyrido[4,3-b]indole (4) (±)-trans-2-tert-butyl-2,3,4,4a,5,9b-hexahydro-5-phenyl-1H-pyrido[4,3-b]indole hydrochloride, m.p. 267° C. (dec)

(5) (±)-trans-2-benzyl-2,3,4,4a,5,9b-hexahydro-5-phenyl-1H-pyrido[4,3-b]indole (6) (±)-trans-2-(4-chlorobenzyl)-2,3,4,4a,5,9b-hexahydro-5-phenyl-1H-pyrido[4,3-b]indole (7) (±)-trans-2-cyclopropyl-2,3,4,4a,5,9b-hexahydro-5-phenyl-1H-pyrido[4,3-b]indole, m.p. 101–102° C (8) (±)-trans-2,3,4,4a,5,9b-hexahydro-2-isopropyl-5-phenyl-1H-pyrido[4,3-b]indole hydrochloride, m.p. 274° C. (dec)

(9) (±)-trans-8-bromo-5-(4-bromophenyl)-2,3,4,4a,5,9b-hexahydro-2-methyl-1H-pyrido[4,3-b]indole, hydrochloride, m.p. 224° C. (dec)

(10) (±)-trans-8-tert-butyl-5-(4-tert-butylphenyl)-2,3,4,4a,5,9b-hexahydro-2-methyl-1H-pyrido[4,3-b]indole

(11) (±)-trans-2,3,4,4a,5,9b-hexahydro-8-methoxy-5-(4-methoxyphenyl)-2-methyl-1H-pyrido[4,3-b]indole

(12) (±)-trans-2,3,4,4a,5,9b-hexahydro-2,8-dimethyl-5-(4-methylphenyl)-1H-pyrido[4,3-b]indole

(13) (±)-trans-2,3,4,4a,5,9b-hexahydro-8-methoxy-5-(4-methoxyphenyl)-2-pentyl-1H-pyrido[4,3-b]indole

(14) (±)-trans-8-chloro-5-(4-chlorophenyl)-2,3,4,4a,5,9b-hexahydro-2-methyl-1H-pyrido[4,3-b]indole

(15) (±)-trans-8-chloro-5-(4-chlorophenyl)-2-cyclopropyl-2,3,4,4a,5,9b-hexahydro-1H-pyrido[4,3-b]indole

(16) (±)-trans-8-bromo-5-(4-bromophenyl)-2-cyclopropyl-2,3,4,4a,5,9b-hexahydro-1H-pyrido[4,3-b]indole hydrochloride, m.p. 236° C. (dec)

(17) (±)-trans-2,3,4,4a,5,9b-hexahydro-2-methyl-5-[3-trifluoromethyl)phenyl]-1H-pyrido[4,3-b]indole, hydrochloride, m.p. 223.5° C (dec)

(18) (±)-trans-2,3,4,4a,5,9b-hexahydro-2-isopropyl-8-methoxy-5-(4-methoxyphenyl)-1H-pyrido[4,3-b]indole

EXAMPLE 2

(±)-trans-2-(cyclobutylmethyl)-2,3,4,4a,5,9b-hexahydro-5-phenyl-1H-pyrido[4,3-b]indole The hydrochloride salt of 2,3,4,5-tetrahydro-5-phenyl-1H-pyrido[4,3-b]indole (8.3 grams, 0.29 moles), prepared by acid catalyzed condensation between 4-piperidone and 1,1-diphenylhydrazine, was suspended in 130 $CHCl_3$ to which was added triethylamine (12.4 ml, 0.090 moles). Aftr stirring several minutes, solution was obtained, then cyclobutanecarbonyl chloride (3.6 grams, .030 moles) in 10 ml $CHCl_3$ was added. The mixture was refluxed for an hour, allowed to cool to room temperature, washed with water, dried over $K_2CO_3$, filtered, and evaporated to dryness in vacuo. The oily residue was dissolved in benzene and filtered through a colunn of neutral alumina. On standing overnight the oil crystallized, yielding 8.2 g. (.025 moles) of 2-(cyclobutylcarbonyl)-2,3,4,5-tetrahydro-5-phenyl-1H-pyrido[4,3-b]indole, m.p. 124° C.

Under a nitrogen atmosphere, the above amide (8.2 g., .025 moles) was dissolved in 130 ml THF, which was freshly chromatographed over neutral alumina. The solution was then added to a 1 molar $BH_3$/THF complex in THF (160 ml, 0.160 moles $BH_3$). The resulting mixture was refluxed about 20 hours. The THF was distilled off on a steam bath under a nitrogen atmosphere. The residue was cooled in an ice bath, then 360 ml of a 1:1 solution of glacial acetic acid and 5N HCl were added, and the mixture was refluxed for 2 hours. The mixture was then poured into a breaker surrounded by an ice bath and made basic by addition of aqueous NaOH. Upon cooling, the oily residue began to solidify. The basic mixture was extracted 5 times with $CHCl_3$. The combined extracts were washed with water until the water was neutral to litmus, then dried with $K_2CO_3$, filtered and evaporated to dryness in vacuo. Upon scratching in an ice bath the residue solidified. Recrystallization from ethanol gave 2.6 g of the title compound, m.p. 76.5°–77° C.

The compounds of Formula I listed in Table II can be prepared in a similar fashion, substituting the appropriate acid chloride for cyclobutanecarbonyl chloride in the acylation step and, where necessary, in the reduction step, using a mixture of 4–5 parts diglyme to 1 part THF at reaction medium to attain a reflux temperature of 95°–105° C. As indicated in Table II, some of the compounds were recovered as the hydrochloride salt, in a manner similar to that described in Example 1.

Table II (1) (±)-trans-2-(cyclopropylmethyl)-2,3,4,4a,5,9b-hexahydro-5-phenyl-1H-pyrido[4,3-b]indole, hydrochloride, m.p. 276–277° C.

(2) (±)-trans-2-(cyclopentylmethyl)-2,3,4,4a,5,9b-hexahydro-5-phenyl-1H-pyrido[4,3-b]indole, m.p. 76–77° C.

(3) (±)-trans-2-(cyclohexylmethyl)-2,3,4,4a,5,9b-hexahydro-5-phenyl-1H-pyrido[4,3-b]indole, hydrochloride, m.p. 273–274° C. (dec)

(4) (±)-trans-2-(1-adamantylmethyl)-2,3,4,4a,5,9b-hexahydro-5-phenyl-1H-pyrido[4,3-b]indole, hydrochloride, m.p. 270° C. (dec)

(5) (±)-trans-2-(furfuryl)-2,3,4,4a,5,9b-hexahydro-5-phenyl-1H-pyrido[4,3-b]indole, hydrochloride, m.p. 241° C. (dec)

(6) (±)-trans-2,3,4,4a,5,9b-hexahydro-5-phenyl-2-(2-thenyl)-1H-pyrido[4,3-b]indole, hydrochloride, m.p. 215° C. (dec)

(7) (±)-trans-2,3,4,4a,5,9b-hexahydro-2-isobutyl-5-phenyl-1H-pyrido[4,3-b]indole, m.p. 100–101.5° C.

(8) (±)-trans-2,3,4,4a,5,9b-hexahydro-2-[(4-methylbicyclo[2.2.2]oct-1-yl)methyl]-5-phenyl-1H-pyrido[4,3-b]indole, hydrochloride, m.p. 257° C. (dec)

(9) (±)-trans-2,3,4,4a,5,9b-hexahydro-2-(exo-7-norcaryl-methyl)-5-phenyl-1H-pyrido[4,3-b]indole, hydrochloride, m.p. 245–247° C. (dec)

(10) (±)-trans-2,3,4,4a,5,9b-hexahydro-2-neopentyl-5-phenyl-1H-pyrido[4,3-b]indole, hydrochloride, m.p. 241° C. (dec.)

(11) (±)-trans-2,3,4,4a,5,9b-hexahydro-2-phenethyl-5-phenyl-1H-pyrido[4,3-b]indole, hydrochloride, m.p. 250° C. (dec)

(12) (±)-trans-2,3,4,4a,5,9b-hexahydro-2-[(trans-2-methylcyclopropyl)methyl]-5-phenyl-1H-pyrido[4,3-b]indole

(13) (±)-trans-2,3,4,4a,5,9b-hexahydro-2-[(1-methylcyclopropyl)methyl]-5-phenyl-1H-pyrido[4,3-b]indole

(14) (±)-trans-2-(2-adamantylmethyl)-2,3,4,4a,5,9b-hexahydro-5-phenyl-1H-pyrido[4,3-b]indole, hydrochloride, m.p. 288° C. (dec)

(15) (±)-trans-2-(1-adamantylmethyl)-8-chloro-5-(4-chlorophenyl)-2,3,4,4a,5,9b-hexahydro-1H-pyrido[4,3-b]indole

(16) (±)-trans-8-chloro-5-(4-chlorophenyl)-2-(cyclohexylmethyl)-2,3,4,4a,5,9b-hexahydro-1H-pyrido[4,3-b]indole

(17) (±)-trans-2-(cyclobutylmethyl)-2,3,4,4a,5,9b-hexahydro-8-methyl-5-(4-methylphenyl)-1H-pyrido[4,3-b]indole

(18) (±)-trans-8-tert-butyl-5-(4-tert-butylphenyl)-2-(cyclopropylmethyl)-2,3,4,4a,5,9b-hexahydro-1H-pyrido[4,3-b]indole

(19) (±)-trans-2-(2-adamantylmethyl)-2,3,4,4a,5,9b-hexahydro-8-methoxy-5-(4-methoxyphenyl)-1H-pyrido[4,3-b]indole

Table II-continued

(20) (±)-trans-2-(1-adamantylmethyl)-2,3,4,4a,5,9b-hexa=
hydro-8-methyl-5-(4-methylphenyl)-1H-pyrido=
[4,3-b]indole

(21) (±)-trans-2-(cyclopentylmethyl)-2,3,4,4a,5,9b-hexa=
hydro-5-[3-(trifluoromethyl)phenyl]-1H-=
pyrido[4,3-b]indole

EXAMPLE 3

(+)-trans-2,3,4,4a,5,9b-hexahydro-5-phenyl-1H-pyrido[4,3-b]indole

A solution of ethyl chloroformate (22 g., 0.2 mole) in 100 ml. dry benzene was added to a solution of (+)-trans-2-cyclopropylmethyl-2,3,4,4a-5,9b-hexahydro-5-phenyl-1H-pyrido[4,3-b]indole (16 g. crude material, prepared as described above, 0.047 moles in theory) in 400 ml. anhydrous benzene with stirring. The resulting mixture was refluxed for 3 hours. As the mixture was refluxing, a whitish solid precipitated. After refluxing, the mixture was cooled and filtered to remove the precipitate, then the filtrate was evaporated to dryness under vacuum, yielding a yellow oil. This oil was dissolved in 400 ml. n-butanol, 40 g of KOH pellets were added, and the resulting mixture was refluxed with stirring for 1 hour. After refluxing, the mixture was cooled, and concentrated under vacuum. Water and toluene were added and the mixture was placed in a separatory funnel. The toluene layer was removed and washed with water until the waste water was neutral to litmus. The toluene layer was then extracted four times with 125 ml. of 1 molar tartaric acid. The combined extracts were then washed once with ether, made basic by addition of 50% aqueous NaOH, cooled, and extracted two times with 75 ml. $CHCl_3$. The $CHCl_3$ extract was washed with water until the wash water was neutral to litmus, dried with $K_2CO_3$, filtered, and evaporated to dryness under vacuum, yielding 9.7 g. of an oil. This was left in a refrigerator overnight, then was triturated with hexane, yielding a solid. Recrystallization from hexane yielded 4.9 g. of the title compound, m.p. 94°–94.7° C.

For the 2-cyclopropylmethyl starting material in Example 3, there can be substituted the corresponding 2-methyl, 2-ethyl, 2-benzyl, 2-methoxybenzyl, 2-methylbenzyl, or 2-chlorobenzyl compound. For the ethyl chloroformate, there can be substituted vinyl chloroformate, any $C_3$-$C_4$ alkyl chloroformate, phenyl chloroformate, benzyl chloroformate, or methyl-, methoxy-, or chlorobenzyl chloroformate.

The representative compounds of Table III can be made in similar fashion, substituting the appropriate starting materials:

Table III (1) (±)-trans-8-bromo-5-(4-bromophenyl)-2,3,4,4a,5,9b-hexa=
hydro-1H-pyrido[4,3-b]indole hydro-
chloride, m.p. 322° C. (dec)

(2) (±)-trans-2,3,4,4a,5,9b-hexahydro-5-[3-(trifluoro=
methyl)phenyl]-1H-pyrido[4,3-b]indole
hydrochloride, m.p. 248.6–249.8° C. (dec)

(3) (±)-trans-8-chloro-5-(4-chlorophenyl)-2,3,4,4a,5,9b-=
hexahydro-1H-pyrido[4,3-b]indole (4) (±)-trans-2,3,4,4a,5,9b-hexahydro-8-methoxy-5-(4-=
methoxyphenyl)-1H-pyrido[4,3-b]indole

EXAMPLE 4

(+)-trans-2-(3-chloro-2-butenyl)-2,3,4,4a,5,9b-hexahydro-5-phenyl-1H-pyrido[4,3-b]indole, hydrochloride To a solution of (+)-trans-2,3,4,4a,5,9b-hexahydro-5-phenyl-1H-pyrido[4,3-b]indole (3 g., 0.012 moles) in 50 ml. dimethylformamide was added 5 ml. triethylamine (0.040 moles). Then 1.6 g. 1.3-dichloro-2-butene (0.013 moles) was added and the mixture was stirred for two hours with formation of a white precipitate. The reaction mixture was then poured into water and extracted into ether. The ether was washed several times with water, dried with $K_2CO_3$, filtered and evaporated to dryness in vacuo. The residue was taken up in benzene, chromatographed through a column of neutral alumina. The resulting oil was taken up in anhydrous ether, ethereal HCl was added and a solid hydrochloride salt formed. Recrystallization from ethanol provided 2.6 g. of the title compound, m.p. 242° C. (dec.).

Table IV is a list of illustrative compounds of Formula I which can be made in similar fashion by substituting the appropriate alkylating agent for the 1,3-dichloro-2-butene.

Table IV (1) (±)-trans-2-allyl-2,3,4,4a,5,9b-hexahydro-5-phenyl-1H-=
pyrido[4,3-b]indole, m.p. 68–68.5° C.

(2) (±)-trans-2,3,4,4a,5,9b-hexahydro-5-phenyl-2-(2-=
propynyl)-1H-pyrido[4,3-b]indole, m.p.
98–98.5° C.

(3) (±)-trans-2,3,4,4a,5,9b-hexahydro-2-(3-methyl-2-=
butenyl)-5-phenyl-1H-pyrido[4,3-b]indole (4) (±)-trans-2-cyclopentyl-2,3,4,4a,5,9b-hexahydro-5-=
phenyl-1H-pyrido[4,3-b]indole hydro=
chloride, m.p. 301.5° C. (dec)

(5) (±)-trans-2-cycloheptyl-2,3,4,4a,5,9b-hexahydro-8-=
methoxy-5-(4-methoxyphenyl)-1H-pyrido=
[4,3-b]indole (6) (±)-trans-2-(2-bromoallyl)-2,3,4,4a,5,9b-hexahydro-8-=
methyl-5-(4-methylphenyl)-1H-pyrido[4,3-b]=
indole (7) (±)-trans-2-(trans-2-butenyl)-8-chloro-5-(4-chloro=
phenyl)-2,3,4,4a,5,9b-hexahydro-1H-pyrido=
[4,3-b]indole (8) (±)-trans-2,3,4,4a,5,9b-hexahydro-8-methoxy-5-(4-=
methoxyphenyl)-2-neopentyl-1H-pyrido[4,3-b]=
indole (9) (±)-trans-2-(2-chlorocinnamyl)-2,3,4,4a,5,9b-hexahydro-=

Table IV-continued 8-methyl-5-(4-methylphenyl)-1H-pyrido=
[4,3-b]indole
(10) (±)-trans-2,3,4,4a,5,9b-hexahydro-2-(3-methoxycinnamyl)-=
5-phenyl-1H-pyrido[4,3-b]indole
(11) (±)-trans-8-bromo-5-(4-bromophenyl)-2,3,4,4a,5,9b-hexa=
hydro-2-(3-phenyl-2-propynyl)-1H-pyrido=
[4,3-b]indole
(12) (±)-trans-8-chloro-5-(4-chlorophenyl)-2,3,4,4a,5,9b-=
hexahydro-2-(3-phenylpropyl)-1H-pyrido=
[4,3-b]indole

EXAMPLE 5

(+)-trans-2-[(3-cyclohexen-1-yl)methyl]-2,3,4,4a,5,9b-hexahydro-5-phenyl-1H-pyrido4,3-b]indole, hydrochloride To a solution of 2.9 g. (+)-trans-2,3,4,4a,5,9b-hexahydro-5-phenyl-1H-pyrido[4,3-b]indole (0.116 moles) in 80 ml. CHCl₃ was added 5 ml. triethylamine (.040 moles) followed by 3-cyclohexene-1-carbonyl chloride (0.126 moles) in 20 ml. CHCl₃. The resulting solution was refluxed overnight (approx. 16 hours), cooled, washed first with water, then with dilute aqueous HCl, then again with water until the wash water was neutral to litmus. The solution was then dried over K₂CO₃, filtered and evaporated to dryness, yielding 3.1 g. of (+)-trans-2[(3-cyclohexen-1-yl)carbonyl]-2,3,4,4a,5,9b-hexahydro-5-phenyl-1H-pyrido[4,3-b]indole.

Under a nitrogen atmosphere, the above amide (3.1 g., 0.0088 moles) dissolved in 250 ml. anhydrous benzene was added dropwise with stirring to a solution composed of 17 ml. of a reducing reagent (70% sodium bis(2-methoxyethoxy)aluminum hydride in benzene) in 100 ml. dry benzene. The mixture was cooled in an ice bath, and 100 ml. of 40% aqueous NaOH was added. The mixture was placed in a separatory funnel. The benzene layer was removed, washed with water until the wash water was neutral to litmus, filtered and evaporated to dryness under vacuum. The residue was taken up in ether, ethereal HCl was added, and a solid precipitated. Recrystallization from acetone yielded 1.1 g. of the title compound, m.p. 241° C. (dec).

Table V is a list of additional illustrative compounds of Formula I which can be made by the procedure of Example 5, substituting the appropriate acyl chloride (or equivalent acylating agent of the formula

supra).

Table V (1) (±)-trans-2,3,4,4a,5,9b-hexahydro-2-[(4-methylbicyclo=
[2.2.2]oct-2-en-1-yl)methyl]-5-phenyl-1H-=
pyrido[4,3-b]indole hydrochloride, m.p.
254° C. (dec)
(2) (±)-trans-[(cis-1,6-dimethyl-endo-3-norcaren-7-yl)=
methyl]-2,3,4,4a,5,9b-hexahydro-5-phenyl-=
1H-pyrido[4,3-b]indole
(3) (±)-trans-2-[(2,3-dimethylcycloprop-2-en-1-yl)methyl]-=
2,3,4,4a,5,9b-hexahydro-5-phenyl-1H-pyrido=
[4,3-b]indole, hydrochloride, m.p. 141° C.
(dec)

Catalytic reduction of compound (3) of Table V with hydrogen on 5% Pd charcoal yields (+)-trans-2-[(cis-2,3-dimethylcyclopropyl)methyl]-2,3,4,4a,5,9b-hexahydro-5-phenyl-1H-pyrido[4,3-b]indole.

EXAMPLE 6

(+)-trans-2-(1-adamantylmethyl)-2,3,4,4a,5,9b-hexahydro-5-phenyl-1H-pyrido[4,3-b]indole A solution of 1-adamantanecarbonyl chloride (4 g., 0.02 moles) in 40 ml. chloroform was added dropwise to a stirred solution of (+)-trans-2,3,4,4a,5,9b-hexahydro-5-phenyl-1H-pyrido[4,3-b]indole (5 g., 0.02 moles) and triethylamine (15 ml., 10 g., 0.10 moles) in 100 ml. chloroform. The solution was refluxed for 45 minutes, cooled, and washed two times with water. The organic layer was dried over K₂CO₃ and the solvent evaporated to give an oil which solidified on trituration under hexane to give 7.52 g. of crude amide, m.p. 211°-213° C.

A solution of this amide (4.1 g., 0.01 moles) in 50 ml. THF was added dropwise to 25 ml. of 1 molar BH₃/THF with stirring under nitrogen. It was then heated to reflux for three hours, cooled in ice, and 25 ml. of con.HCl was cautiously added. The mixture was then refluxed for another three hours and allowed to stand overnight at room temperature forming a voluminious white precipitate. This mixture was basified with 25 ml. of 50% NaOH and sufficient water was added to dissolve the salts. Two clear phases were obtained. The upper phase is evaporated to dryness and the lower (aqueous) phase was extracted with chloroform. This chloroform was then used to take up the residue from the evaporated upper THF layer. The combined organic extracts were washed with water and dried over K₂CO₃. The evaporation of solvent and recrystallization of residue from 50 ml. ethanol gave 2.7 g. of the title compound, m.p. 117°-119° C. which gas chromatograhic analysis showed to be greater than 99.9% pure.

Biological Tests

Compounds of this invention have been evaluated for pharmacological activity in the following tests:

Analgesic

Phenylquinone Writhing (PQW):

results given in: mg/kg po/mouse

Groups of at least 10 mice are given phenyl-p-benzoquinone 2.5 mg/kg intraperitoneally 30 minutes after oral administration of graded doses of the test substance. Two or more dose levels are used for each compound. For scoring purposes, a "writhe" is defined as stretching, twisting of a hindleg inward, or contraction of the abdomen. The total number of writhes for each animal, treated and control animals, side-by-side, are counted over a 30-minute time interval. An $ED_{50}$, calculated on basis of the percentage of animals at each dose level which showed 50% or less of the average number of writhes of the control animals, is reported for each compound submitted to this screening test. The PQW test is widely used as an indicator of potential analgesic activity in man, especially for non-narcotic substances.

Sedative

Decreased Locomotor Activity (LMA):

results given in: mg/kg po/mouse

This reaction sign is measured subjectively by observing how an animal behaves when it is removed from an observation cage and placed on a table top. Untreated animals will immediately begin active exploration of their environment. Animals that have received a depressant compound will show a gradually decreasing responsiveness to a new environment. The degree of stimulation by the observer needed to product active locomotion is rated on an arbitrary scale. This ranges from a score of −1 where only a slight touch of the animal's body is required to a −4 where the animal is unresponsive or minimally responsive to the application of a pain stimulus (pressure at the base of the tail). The minimal effective dose (MED) is the lowest oral dose producing an obvious decrease of locomotor activity (with a score of at least −1). Groups of 3 mice are given decreasing oral doses at 0.5 log intervals (300, 100, 30 ... etc.) until no behavioral effects are evident. Decrease of locomotor activity is indicative of general central nervous system depressant activity.

Major Tranquilizer

Rat Conditioned Avoidance Response (CAR):

results given in: mg/kg po/rat

Rats are trained to jump out of a pit onto a ledge to avoid shock when presented with a light and sound conditioned stimulus. The animals are tested 1, 2, and 4 hours after administration of the test compound. Three to four dose levels and groups of 4–8 animals/dose are used. The $ED_{50}$ is the dose producing a block of the CAR in 50% of the animals. Blocking of the CAR at non-toxic doses appears to correlate with major tranquilizer (antipsychotic) activity in man.

Minor Tranquilizer

Rat Conflict (Approach-Avoidance) Test(Conf)

results given in: mg/kg po/rat

Food-deprived rats are trained to pass from one compartment to an adjacent one to obtain food. The training consists of three exposures to the test situation on day one of the experiment. The rats are given limited (1–2 hrs.) free access to food in their home cages on day one and are then food deprived for at least 18 hours. On day two of the experiment, the rats are given a control exposure to the test situation followed by a second exposure after ½ to 1 hour in which they are shocked after crossing and eating. Groups of 6–8 rats are then dosed orally with solvent or test compound and then re-exposed to the test situation after 1 or 2 hours.

Compounds showing minor tranquilizer (anxiolytic) activity in man such as diazepam and meprobamate produce an apparent decreased fear in the test animals so that they cross to obtain food despite having received a shock earlier. This effect is dose-related (and the MED is the minimum dose at which this effect is obtained); rats dosed with solvent only consistently show a high level of fear as evidenced by decreased mobility and absence of feeding when placed in the test situation after receiving a shock.

Muscle Relaxant

Etonitazene Antagonism Test (EA):

Etonitazene is a potent narcotic compound. The etonitazene antagonism test is used to evaluate the ability of new chemical compounds to antagonize the increased muscle tone produced by the narcotic compound. One hour after oral administration of a test compound to mice, 20 mcg/kg etonitazene is given by the subcutaneous route. Thirty minutes after administration of etonitazene, the mice are examined for the presence of Straub tail. The abdominal musculature is also palpated to determine the degree of tone relative to control animals run at the same time. Compounds with potential muscle relaxant activity (e.g., chlorpromazine, diazepam) will antagonize the increased muscle tone and/or Straub tail in a dose-related manner.

Hypotensive (Hypo)

The ability of the compounds to lower the blood pressure in conscious rats is determined by recording the rat blood pressure directly via cannulation of the tail artery. The oral dose which produces a significant fall in blood pressure is recorded.

Adrenergic Blockage (AB)

Dogs are prepared for direct recording of blood pressure from a cannula in the femoral artery. Drugs are administered intraveneously through a cannula in the femoral vein. The ability of compounds to block the pressor response to epinephrine and/or nor-epinephrine is recorded at various doses.

Results obtained in the foregoing tests for compounds of this invention are shown in the following table. Results in the pertinent tests are also shown for chlorpromazine (a major tranquilizer) diazepam (a minor tranquilizer) and codeine phosphate and aspirin (analgesics).

Table VI

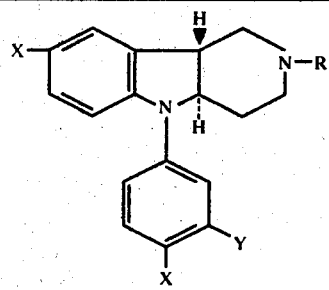

| Compound* R | PQW mouse $ED_{50}$ | LMA mouse MED | CAR rat $ED_{50}$ | Conf rat MED | EA mouse | Hypo rat MED | AB dog MED |
|---|---|---|---|---|---|---|---|
| —CH₃ | 4 | 10 | 5 | 1 | — | 30 | 0.01 |
| —C₂H₅ | 1 | 1 | 6 | NT | + | NT | NT |
| —CH(CH₃)₂ | 2.6 | 14 | NT | NT | + | NT | NT |
| —C(CH₃)₃ | 40 | NT | NT | NT | NT | NT | NT |
| —CH₂—CH(CH₃)₂ | 4 | 10 | NT | NT | — | NT | NT |
| —CH₂-cyclopropyl | 3 | 3 | NT | NT | — | NT | NT |
| —CH₂-cyclobutyl | 2 | 3 | 4 | 1 | + | 3 | 0.10 |
| —CH₂-cyclopentyl | 1 | 10 | 5 | 1 | — | 10 | 0.03 |
| —CH₂-cyclohexyl | 4 | 3 | 20 | 1 | + | 10 | 0.03 |
| —CH₂—C≡CH | 3 | 30 | NT | NT | + | NT | NT |
| —CH₂—CH=CH₂ | 4 | 10 | NT | NT | — | NT | NT |
| —CH₂-(1-methyladamantyl) | 80 | 30 | NT | NT | + | NT | NT |
| —CH₂-norbornyl | 1 | 0.1 | NT | NT | + | NT | NT |
| —CH₂-adamantyl | 19 | 30 | 50 | 10 | — | NT | >1 |
| CH₂-(2-adamantyl) | 27 | 2 | NT | 10** | + | NT | NT |
| —CH₂—CH=C(Cl)CH₃ | 2 | 1 | NT | NT | + | NT | NT |
| —CH₂—CH₂—C₆H₅ | 2 | 10 | NT | NT | + | NT | NT |
| —CH₂-(1-methylbicyclo[2.2.2]octyl) | 14 | 30 | NT | NT | — | NT | NT |
| —CH₂—C(CH₃)₃ | 13 | 30 | NT | NT | — | NT | NT |

Table VI-continued

[Structure: substituted pyrido[4,3-b]indole with X, Y, and N-R substituents]

| Compound* R | PQW mouse $ED_{50}$ | LMA mouse MED | CAR rat $ED_{50}$ | Conf rat MED | EA mouse | Hypo rat MED | AB dog MED |
|---|---|---|---|---|---|---|---|
| —CH₂—(cyclohexenyl) | 2 | 3 | NT | NT | + | NT | NT |
| —H | 0.9 | 30 | >100 | NT | − | NT | NT |
| (cyclopropyl) | 21 | 10 | NT | NT | − | NT | NT |
| (cyclopentyl) | 7.7 | 10 | NT | NT | + | NT | NT |
| —CH₃ (X = Br, Y = H) | 2.5 | 3 | 4 | NT | − | NT | 0.1 |
| —H (X = Br, Y = H) | 19 | 10 | NT | NT | − | NT | NT |
| —CH₃ (X = H, Y = CF₃) | 24 | 100 | NT | NT | − | NT | NT |
| STANDARD COMPOUNDS | | | | | | | |
| chlorpromazine | | 2–10 | 6 | I | | | |
| diazepam | | 3–10 | Ia | 3–10ª | | | |
| codeine phosphate | 19 | | | | | | |
| aspirin | 94 | | | | | | |

I - minimal or no activity
NT - Not tested
Ia - inactive at doses not producing ataxia
a - active, but also causes ataxia at this dose
* - except as otherwise indicated X = Y = H
** - active at this dose; MED not yet determined

Formulation and Administration

For analgesia, compounds of this invention can be administered to warm-blooded animals orally or rectally at a level of about 0.1 to 10 milligrams per kilogram of body weight, 4 to 6 times a day as necessary. Water-soluble salts of the compounds can be administered by subcutaneous or intramuscular injection at a level of about 0.05 to 5 mg/kg of body weight, 4 to 6 times a day as necessary. For the preferred analgesic, trans-2,3,4,4a,5,9b-hexahydro-5-phenyl-1H-pyrido[4,3-b]indole, the corresponding preferred ranges are about 0.1 to 1 mg/kg orally or rectally and about 0.05 to 0.5 mg/kg parenterally.

For sedation, trans-2,3,4,4a,5,9b-hexahydro-2(exo-7-norcarylmethyl]-5-phenyl-1H-pyrido[4,3-b]indole can be administered to warm-blooded animals orally or rectally at a level of about 0.1 to 2 mg/kg. Its water soluble salts can be administered parenterally at a level of about 0.05 to 1 mg/kg. The other less active compounds can be used for sedation at proportionately higher doses. The dosage can be repeated 3 to 6 times a day as necessary.

For minor tranquilizing activity in humans, trans-2-(1-adamantylmethyl)-2,3,4,4a,5,9b-hexahydro-5-phenyl-1H-pyrido4,3-b]indole and trans-2-(2-adamantylmethyl)-2,3,4,4a,5,9b-hexahydro-5-phenyl-1H-pyrido[4,3-b]indole can be administered orally or rectally at about 0.1 to 10 mg/kg of body weight. Its water-soluble salts can be administered parenterally at about 0.05 to 5 mg/kg of body weight. The dosage can be repeated 3 to 6 times a day as necessary.

For major tranquilizing activity in humans, trans-2-(cyclobutylmethyl)- and trans-2-(cyclopentylmethyl)-2,3,4,4a,5,9b-hexahydro-5-phenyl-1H-pyrido[4,3-b]indole and trans-8-bromo-5-(4-bromophenyl)-2,3,4,4a,5,9b-hexahydro-2-methyl-1H-pyrido[4,3-b]indole can be administered orally or rectally at about 0.1 to 5 mg/kg of body weight. Their water-soluble salts can be administered parenterally at about 0.05 to 3 mg/kg of body weight. The dosage can be repeated 3 to 6 times a day as necessary.

The probable human dose for analgesics can be estimated by comparing the animal analgesic dose for the compound of this invention to the dose of a standard drug in the same animal system. For example, the compound of Example 3 is shown to have analgesic activity compared to codeine and aspirin:

|  | Analgesic Dose (mice) | Usual Analgesic dose (humans) |
|---|---|---|
| codeine phosphate | 19 mg/kg | 15–300 mg/day |
| aspirin | 94 mg/kg | 300–8000 mg/day |
| compound of Example 3 | 1 mg/kg | 1–80 mg/day |

Since the compound of Example 3 is about 20 times more potent than codeine and almost 100 times as potent as aspirin, its human dose can be about 1–80 mg/day, i.e., about 1/20 the codeine dose or 1/100 the aspirin dose.

Dosage forms for the compound of Example 3 will usually contain between 1 and 20 mg of the active ingredient. However, lower or higher strengths may be required depending on the age and condition of the patient being treated, the severity of pain, and the frequency of treatment required.

Similarly, by comparing the effects of standard CNS drugs such as chlorpromazine and diazepam in the same animal systems as the compounds of this invention the strength of dosage forms for human use may be determined.

|  | Rat CAR | Rat Conf. | Usual Human Dose | Dosage Form Strength |
|---|---|---|---|---|
| chlorpromazine | 6 mg/kg | — | 10–1000 mg/day | 10–200 mg tablets 25 mg/ml injection 0.2% syrup |
| diazepam | — | 3–10 mg/kg | 4–40 mg/day | 2–10 mg/tablet 5 mg/ml injection |
| compound 4 of Table II | — | 10 mg/kg | 5–50 mg/day | 2.5–25 mg/dose |
| compound of Example 2 | 4 mg/kg | — | 5-500 mg/day | 5–100 mg/dose |

The compounds can be formulated into compositions comprising a compound of Formula I or a pharmaceutically suitable acid addition salt thereof together with a pharmaceutically suitable carrier. The carrier can be either a solid or liquid, and the compositions can be in the form of tablets, liquid-filled capsules, dry filled capsules, aqueous solutions, non-aqueous solutions, suppositories, syrups, suspensions, and the like. The compositions can contain suitable preservatives, coloring and flavoring agents. Some examples of the carriers which can be used in the preparation of the products of the invention are gelatin capsules; sugars such as lactose and sucrose; starches, dextrans and cellulosics, such as methyl cellulose; cellulose acetate phthalate; gelatin; talc; stearic acid salts; vegetable oils such as peanut oil, cottonseed oil, sesame oil, olive oil, corn oil, and oil of theobroma; liquid petrolatum; polyethylene glycol; glycerine; sorbitol; propylene glycol; ethanol; agar; water, and isotonic saline.

In formulating the compounds, conventional practices and precautions are used. The composition intended for enteral administration must be sterile, and this can be assured either by using sterile ingredients and carrying out the production under aseptic conditions, or by sterilizing the final composition by one of the usual procedures such as autoclaving under appropriate temperature and pressure conditions. Customary care should be exercised that no incompatible conditions exist between the active components and the diluent, preservative or flavoring agent or in the conditions employed in preparation of the compositions.

Typical formulations of the type listed above which may be used for the administration of these compounds are:

EXAMPLE A

| Ingredients | mg/tablet |
|---|---|
| trans-2,3,4,4a,5,9b-hexahydro-5-phenyl-1H-pyrido[4,3-b]indole | 15 mg |
| lactose, USP | 185 mg |

All of the above ingredients are passed through a suitable sieve, blended for 20 minutes, and compressed directly into tablets of 200 mg on a suitable tablet press using a 11/32" punch and die.

EXAMPLE B

| Ingredients | mg/tablet |
|---|---|
| trans-2,3,4,4a,5,9b-hexahydro-2-(exo-7-norcarylmethyl)-5-phenyl-1H-pyrido[4,3-b]indole | 50 mg |
| lactose, USP | 215 mg |
| methylcellulose, USP | 15 mg |
| talc, USP | 6 mg |
| starch, USP | 10 mg |
| magnesium stearate, USP | 4 mg |
| color (if desired) | q.s. |

The lactose and active ingredient are wet granulated with a solution of methylcellulose in a blender until a satisfactory mass is achieved. The mass is dried and classified through an appropriate sieve. The remaining ingredients are passed through an 80 mesh sieve and blended with the dried granulated material. The blend is then compressed into tablets on a suitable tablet press at a weight of 300 mg using a ⅜ inch punch and die.

EXAMPLE C

| Ingredients | mg/capsule |
|---|---|
| trans-2-(1-adamantylmethyl)-2,3,4,4a,5,9b-hexahydro-5-phenyl-1H-pyrido[4,3-b]indole | 25 mg |
| lactose, USP | 100 mg |
| magnesium stearate, USP | 1 mg |
| colloidal silicon dioxide, N.F. | 2 mg |

The combined ingredients are blended and passed through a 40 mesh sieve, and the mixture is encapsulated into a two-piece hard gelatin No. 3 capsule on a suitable encapsulating machine at a net weight of 128 mg.

EXAMPLE D

| Ingredients | gram/liter |
|---|---|
| (±)-trans-2-ethyl-2,3,4,4a,5,9b-hexahydro-5-phenyl-1H-pyrido[4,3-b]indole hydrochloride | 3 g |
| granulated sugar | 600 g |
| sodium benzoate | 1 g |
| flavor | q.s. |
| color | q.s. |

| Ingredients | gram/liter |
| --- | --- |
| deionized water | q.s. |

All of the above ingredients are dissolved in water and made up to a volume of one liter.

EXAMPLE E

| Ingredients | gram/liter |
| --- | --- |
| (±)-trans-2,3,4,4a,5,9b-hexahydro-2-methyl-5-phenyl-1H-pyrido[4,3-b]indole hydrochloride | 10 g |
| propylparaben, USP | 0.2 g |
| methylparaben, USP | 1.8 g |
| Water for injection | q.s. to 1 liter |

Dissolve the parabens in about 800 ml of Water for Injection at 80°. Cool to room temperature, add the active ingredient, and stir to dissolve. If the solution is aseptically prepared, sterile filtration through a millipore filter or other suitable retentive filter is required. Terminal sterilization by autoclaving may also be employed to render the product sterile.

What is claimed is:

1. A compound of the formula

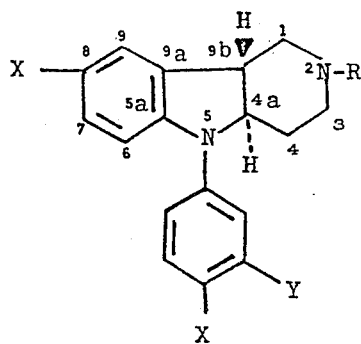

and their pharmaceutically suitable salts, where the hydrogens attached to the carbon atoms in the 4a and 9b positions are in trans relationship to each other, and where:
when Y is —H, X is —H, —Cl, —Br, —CH$_3$, -tert-C$_4$H$_9$ or —OCH$_3$; and
when Y is —CF$_3$, X is —H; and
R is hydrogen; 3-chloro-2-butenyl; 2-bromoallyl; benzyl; benzyl ring-substituted with methyl, methoxy or chloro; phenethyl; 3-phenylpropyl; 3-phenylpropyl ring-substituted with chloro, bromo, or methoxy; furfuryl; 2-thenyl; C$_1$–C$_5$ alkyl; C$_3$–C$_5$ alkenyl; C$_3$–C$_5$ alkynyl; cinnamyl; cinnamyl ring-substituted with chloro, bromo, or methoxy; 3-phenyl-2-propynyl; C$_3$–C$_7$ cycloalkyl; C$_4$–C$_8$ cycloalkylmethyl; (methylcyclopropyl)methyl; (cis-2,3-dimethylcyclopropyl)methyl; C$_6$–C$_8$ cycloalkenylmethyl; C$_6$–C$_8$ cycloalkadienylmethyl; (2,3-dimethylcycloprop-2-en-1-yl)methyl; exo-7-norcarylmethyl; (cis-1,6-dimethyl-endo-3-norcaren-7-yl)methyl; (4-methylbicyclo[2.2.2]oct-1-yl)methyl; (4-methylbicyclo[2.2.2]oct-2-en-1-yl)methyl; (bicyclo[2.2.2]hept-2-yl)methyl; (bicyclo[2.2.2]hept-2-en-5-yl)methyl; 1-adamantylmethyl; or 2-adamantylmethyl.

2. A compound of claim 1 wherein:
X is hydrogen or bromine, and
R is hydrogen, 3-chloro-2-butenyl, phenethyl, furfuryl, 2-thenyl, C$_1$–C$_5$ alkyl, allyl, propynyl, C$_3$–C$_5$ cycloalkyl, C$_4$–C$_7$ cycloalkylmethyl, C$_7$ cycloalkenylmethyl, (2,3-dimethylcycloprop-2-en-1-yl)methyl, exo-7-norcarylmethyl, (4-methylbicyclo[2.2.2]oct-1-yl)methyl, (4-methylbicyclo[2.2.2]oct-2-en-1-yl)methyl, 1-adamantylmethyl or 2-adamantylmethyl.

3. A compound of claim 2 wherein:
Y is hydrogen, and
R is hydrogen, methyl, ethyl, cyclobutylmethyl, cyclopentylmethyl, exo-7-norcarylmethyl, 1-adamantylmethyl or 2-adamantylmethyl.

4. A compound of claim 3 wherein:
X is hydrogen.

5. Compound of claim 2: (+)-trans-2,3,4,4a,5,9b-hexahydro-5-[3-(trifluoromethyl)phenyl]-1H-pyrido[4,3-b]indole.

6. Compound of claim 3: (+)-trans-8-bromo-4-(4-bromophenyl)-2,3,4,4a,5,9b-hexahydro-2-methyl-1H-pyrido[4,3-b]indole.

7. Compound of claim 4: (+)-trans-2-(cyclopentylmethyl)-2,3,4,4a,5,9b-hexahydro-5-phenyl-1H-pyrido[4,3-b]indole.

8. Compound of claim 4: (+)-trans-2,3,4,4a,5,9b-hexahydro-5-phenyl-1H-pyrido[4,3-b]indole.

9. Compound of claim 4: (+)-trans-2,3,4,4a,5,9b-hexahydro-2-(exo-7-norcarylmethyl)-5-phenyl-1H-pyrido[4,3-b]indole.

10. Compound of claim 4: (+)-trans-2-(cyclobutylmethyl)-2,3,4,4a,5,9b-hexahydro-5-phenyl-1H-pyrido[3,2-b]indole.

11. Compound of claim 4: (+)-trans-2-(1-adamantylmethyl)-2,3,4,4a,5,9b-hexahydro-5-phenyl-1H-pyrido[4,3-b]indole.

12. Compound of claim 4: (+)-trans-2-ethyl-2,3,4,4a,5,9b-hexahydro-5-phenyl-1H-pyrido[4,3-b]indole.

13. Compound of claim 4: (+)-trans-2-(2-adamantylmethyl)-2,3,4,4a,5,9b-hexahydro-5-phenyl-1H-pyrido[4,3-b]indole.

14. Pharmaceutical composition consisting essentially of a pharmaceutically suitable vehicle and an effective amount of an analgesic compound of claim 1.

15. Method for producing an analgesic effect in a warm-blooded animal which comprises administering to said animal an effective amount of an analgesic compound of claim 1.

16. Method for causing a tranquilizer effect in a warm-blooded animal by administering to said animal an effective amount of a compound of claim 3 where:
when X is hydrogen, R is ethyl, cyclobutylmethyl, cyclopentylmethyl, 1-adamantylmethyl, or 2-adamantylmethyl, and
when X is bromine, R is methyl.

17. Method of claim 16 wherein the tranquilizer effect is an antipsychotic effect.

18. Method of claim 16 where the tranquilizer effect is an anxiolytic effect and the compound is one where R is 1-adamantylmethyl or 2-adamantylmethyl.

* * * * *

UNITED STATES PATENT OFFICE
CERTIFICATE OF CORRECTION

PATENT NO. : 3,991,199
DATED : NOVEMBER 9, 1976
INVENTOR(S) : JOEL GILBERT BERGER

It is certified that error appears in the above-identified patent and that said Letters Patent are hereby corrected as shown below:

At all of the following places, the prefix "(+)" should be replaced by the prefix "(±)" :

column 11, line 26;

column 13, line 24;

column 15, line 3;

column 17, lines 11 and 16;

column 18, lines 28 and 31;

column 19, lines 15, 18, 28 and the last line;

column 20, lines 17 and 21; and claims 5-13, line 1 of each.

At column 15, line 10, "130" should be -- 130 ml -- .

Signed and Sealed this

Tenth Day of May 1977

[SEAL]

Attest:

RUTH C. MASON
Attesting Officer

C. MARSHALL DANN
Commissioner of Patents and Trademarks